(12) United States Patent
Nabutovsky et al.

(10) Patent No.: US 7,546,159 B1
(45) Date of Patent: Jun. 9, 2009

(54) SUBCUTANEOUS CARDIAC STIMULATION DEVICE, SYSTEM, AND METHOD PROVIDING ACCELERATED ARRHYTHMIA DETECTION VERIFICATION AND TRANSIENT RATE COMPENSATION

(75) Inventors: Yelena Nabutovsky, Mountain View, CA (US); Taraneh Ghaffari Farazi, San Jose, CA (US); Anders Bjorling, Jarfalla (SE); Kjell Noren, Solna (SE)

(73) Assignee: Pacesetter, Inc., Sunnyvale, CA (US)

( * ) Notice: Subject to any disclaimer, the term of this patent is extended or adjusted under 35 U.S.C. 154(b) by 671 days.

(21) Appl. No.: 11/080,215

(22) Filed: Mar. 14, 2005

(51) Int. Cl.
*A61N 1/39* (2006.01)
(52) U.S. Cl. ............................. 607/7; 607/14
(58) Field of Classification Search ............... None
See application file for complete search history.

(56) References Cited

U.S. PATENT DOCUMENTS

| | | |
|---|---|---|
| 4,686,988 A | 8/1987 | Sholder |
| 4,708,142 A | 11/1987 | DeCote, Jr. |
| 4,712,555 A | 12/1987 | Thornander et al. |
| 4,729,376 A | 3/1988 | DeCote, Jr. |
| 4,766,902 A | 8/1988 | Schroeppel |
| 4,788,980 A | 12/1988 | Mann et al. |
| 4,809,697 A | 3/1989 | Causey, III et al. |
| 4,907,593 A | 3/1990 | Rapach et al. |
| 4,940,052 A | 7/1990 | Mann et al. |
| 4,944,298 A * | 7/1990 | Sholder ........................ 607/14 |
| 4,944,299 A | 7/1990 | Silvian |
| 4,969,467 A | 11/1990 | Callaghan et al. |
| 5,040,534 A | 8/1991 | Mann et al. |
| 5,313,953 A | 5/1994 | Yomtov et al. ............... 128/696 |
| 5,350,410 A | 9/1994 | Kleks et al. |
| 5,405,363 A | 4/1995 | Kroll et al. |
| 5,447,519 A * | 9/1995 | Peterson ........................ 607/5 |
| 5,454,836 A | 10/1995 | Van der Veen et al. |
| 5,814,076 A | 9/1998 | Brownlee |
| 6,275,734 B1 | 8/2001 | McClure et al. |
| 6,409,675 B1 | 6/2002 | Turcott |
| 6,466,821 B1 | 10/2002 | Pianca et al. |
| 6,477,406 B1 | 11/2002 | Turcott |

(Continued)

FOREIGN PATENT DOCUMENTS

EP 0578748 B1 5/1996

(Continued)

OTHER PUBLICATIONS

Non-Final Office Action mailed Sep. 26, 2006: Related U.S. Appl. No. 10/998,026.

(Continued)

*Primary Examiner*—Carl H. Layno
*Assistant Examiner*—Jon-Eric C. Morales
(74) *Attorney, Agent, or Firm*—Steven M. Mitchell

(57) ABSTRACT

A subcutaneous cardiac stimulation system verifies accelerated arrhythmia detection before delivering accelerated arrhythmia therapy to the heart. The stimulation system includes a verification circuit that verifies detection of the accelerated arrhythmia with each of first and second sense channels utilizing first and second electrode configurations. The therapy circuit delivers the stimulation therapy to the heart if the accelerated arrhythmia detection is verified with each of the first and second electrode configurations. The system also compensates for transient rate changes during the detection of the accelerated arrhythmia.

19 Claims, 6 Drawing Sheets

U.S. PATENT DOCUMENTS

| | | |
|---|---|---|
| 6,491,639 B1 | 12/2002 | Turcott |
| 6,527,729 B1 | 3/2003 | Turcott |
| 6,609,023 B1 * | 8/2003 | Fischell et al. .............. 600/515 |
| 6,625,493 B2 | 9/2003 | Kroll et al. |
| 6,658,292 B2 | 12/2003 | Kroll et al. |
| 7,027,858 B2 | 4/2006 | Cao et al. |
| 7,194,304 B1 * | 3/2007 | Bornzin et al. ................. 607/7 |
| 2002/0165587 A1 | 11/2002 | Zhang et al. |
| 2003/0097153 A1 | 5/2003 | Bardy et al. |
| 2003/0171661 A1 | 9/2003 | Tong |
| 2003/0204215 A1 | 10/2003 | Gunderson et al. |
| 2004/0064177 A1 | 4/2004 | Bardy et al. ................ 607/129 |
| 2004/0230243 A1 | 11/2004 | Haefner et al. |
| 2005/0115561 A1 * | 6/2005 | Stahmann et al. ...... 128/200.24 |
| 2005/0119708 A1 | 6/2005 | Haefner |
| 2005/0288600 A1 * | 12/2005 | Zhang et al. ................ 600/510 |

FOREIGN PATENT DOCUMENTS

| | | |
|---|---|---|
| EP | 0941695 B1 | 11/2003 |
| WO | 03/039668 A1 | 5/2003 |

OTHER PUBLICATIONS

Non-Final Office Action mailed Mar. 16, 2007: Related U.S. Appl. No. 10/998,026.

Final Office Action mailed Aug. 23, 2007: Related U.S. Appl. No. 10/998,026.

Non-Final Office Action mailed Nov. 8, 2007: Related U.S. Appl. No. 10/998,026.

Notice of Allowance mailed May 22, 2008: Related U.S. Appl. No. 10/998,026.

Non-Final Office Action mailed Aug. 6, 2007: Related U.S. Appl. No. 10/998,027.

Non-Final Office Action mailed Jun. 2, 2008: Related U.S. Appl. No. 10/998,027.

Notice of Allowance mailed Jan. 8, 2008: Related U.S. Appl. No. 10/998,027.

Notice of Allowance mailed Sep. 15, 2008: Related U.S. Appl. No. 10/998,027.

* cited by examiner

SUBCUTANEOUS CARDIAC STIMULATION DEVICE, SYSTEM, AND METHOD PROVIDING ACCELERATED ARRHYTHMIA DETECTION VERIFICATION AND TRANSIENT RATE COMPENSATION

FIELD OF THE INVENTION

The present invention generally relates to a cardiac stimulation system that provides electrical therapy to a patient's heart. The present invention more particularly relates to a subcutaneous defibrillation device, system and method that provides accelerated arrhythmia detection verification and transient heart rate compensation.

BACKGROUND OF THE INVENTION

Implantable cardiac devices are well known in the art. They may take the form of implantable cardiac defibrillators or cardioverters (ICDs) which treat accelerated rhythms of the heart such as fibrillation or implantable pacemakers which maintain the heart rate above a prescribed limit, such as, for example, to treat a bradycardia. Implantable cardiac devices are also known which incorporate both a pacemaker and a defibrillator.

A pacemaker may be considered as a pacing system. The pacing system is comprised of two major components. One component is a pulse generator which generates the pacing stimulation pulses and includes the electronic circuitry and the power cell or battery. The other component is the lead, or leads, having electrodes which electrically couple the pacemaker to the heart. A lead may provide both unipolar and bipolar pacing and/or sensing electrode configurations.

Pacemakers deliver pacing pulses to the heart to cause the stimulated heart chamber to contract when the patient's own intrinsic rhythm fails. To this end, pacemakers include sensing circuits that sense cardiac activity for the detection of intrinsic cardiac events such as intrinsic atrial events (P waves) and intrinsic ventricular events (R waves). By monitoring such P waves and/or R waves, the pacemaker circuits are able to determine the intrinsic rhythm of the heart and provide stimulation pacing pulses that force atrial and/or ventricular depolarizations at appropriate times in the cardiac cycle when required to help stabilize the electrical rhythm of the heart.

Implantable cardiac defibrillators are encapsulated in a conductive housing or enclosure. They are generally implanted in a pectoral region of a patient and also electrically connected to the heart with one or more electrode carrying leads implanted in the heart. An arrhythmia detector detects accelerated arrhythmias, such as ventricular tachycardia (VT) or ventricular fibrillation (VF). When such an accelerated arrhythmia is detected, a pulse generator delivers electrical therapy to the patient's heart. A therapy for tachycardia may be anti-tachycardia pacing and a therapy for fibrillation may be a defibrillation shock. Such therapies are well known.

The devices discussed thus far are fully implantable. They are fully implantable because the device enclosures are placed beneath the skin of the patient and the electrodes of the leads are positioned within the heart.

Subcutaneous cardiac stimulation devices and systems are also known in the art. These devices may also be implanted beneath the skin of a patient external to the heart. However, in these systems, the electrodes are not implanted within the heart. Rather, the electrodes are still placed beneath the skin of the patient but external to the heart.

There is a growing role for extravascular and extracardiac ICD implantation of subcutaneous ICDs. These devices are generally easier to implant than fully implantable devices and systems. Subcutaneous devices may be implanted in centers/sites that lack fluoroscopic capability. They should also be less expensive than their fully implantable counterparts.

Unfortunately, diagnosing VT/VF from subcutaneous electrodes spatially removed from the heart is challenging due to interference from non-cardiac signals, such as skeletal myopotentials, motion artifact, etc. Since treatment of VF requires high voltage therapy, which can be extremely painful for the patient, VF detection should be thoroughly verified before making a final diagnosis. Detection however must be sufficiently robust to adapt to a cardiac signal that may include interference not seen in traditional defibrillators having electrodes within the heart.

Ventricular fibrillation (VF) detection from remote sensing electrodes can be accomplished using two separate criteria, as, for example, disclosed in U.S. Pat. No. 7,403,813, filed Nov. 24, 2004, entitled SYSTEMS AND METHODS FOR DETECTION OF VT AND VF FROM REMOTE SENSING ELECTRODES, which application is fully hereby incorporated herein by reference. VF can be diagnosed when either no activity is being detected or when the activity detected has very high rates. The former case applies when the sensed signal amplitude suddenly drops at VF initiation, preventing a detector from sensing the signal. The latter applies when the signal amplitude does not drop, but the rate increases. In many cases the amplitude of the signal varies significantly, complicating the detection.

Hence, the present invention is generally concerned with thoroughly verifying arrhythmia detection before delivering therapy and appropriately compensating for abrupt changes in detected cardiac rate.

SUMMARY OF THE INVENTION

The invention provides a subcutaneous cardiac stimulation system that verifies accelerated arrhythmia detection. The system comprises an arrhythmia detector that detects an accelerated arrhythmia of a heart, and a subcutaneous lead system coupled to the arrhythmia detector and defining first and second arrhythmia detection electrode configurations. The system further comprises a verification circuit that verifies detection of an accelerated arrhythmia with each of the first and second arrhythmia detection electrode configurations, and a therapy circuit that delivers stimulation therapy to the heart responsive to verification of an accelerated arrhythmia with each of the first and second arrhythmia detection electrode configurations.

The verification circuit first verifies an accelerated arrhythmia detection with a first one of the first and second arrhythmia detection electrode configurations. The verification circuit first verifies an accelerated arrhythmia detection with the first one of the first and second accelerated arrhythmia detection electrode configurations during a first verification time period following the first detection of the accelerated arrhythmia.

The verification system preferably further verifies the accelerated arrhythmia detection with both the first and second accelerated arrhythmia detection electrode configurations during a further verification period following the first verification period. The therapy circuit delivers the stimulation therapy to the heart following the further verification.

The verification circuit may verify the accelerated arrhythmia detection during the further verification period with a second one of the first and second accelerated arrhythmia detection electrode configurations providing continuous accelerated arrhythmia detection verification during a verification window within the further verification period. The verification window may be a floating window. The further verification may be completed upon continuous verification with the first one of the first and second accelerated arrhythmia detection electrode configurations up to completion of the verification window. The accelerated arrhythmia may be ventricular fibrillation and/or ventricular tachycardia. The verification circuit may verify detection of an accelerated arrhythmia based upon heart rate and one or more of absence of asystole, and measured myopotential.

The invention further provides a subcutaneous cardiac stimulation system comprising an arrhythmia detector that detects an accelerated arrhythmia of a heart and a subcutaneous lead system coupled to the arrhythmia detector and defining first and second arrhythmia detection electrode configurations. The system further comprises a verification circuit that verifies detection of an accelerated arrhythmia with the first and second arrhythmia detection electrode configurations during successive first and second verification time periods, and a therapy circuit that delivers stimulation therapy to the heart responsive to verification of an accelerated arrhythmia with each of the first and second arrhythmia detection electrode configurations.

The invention further provides a method of verifying subcutaneous cardiac accelerated arrhythmia detection. The method comprises confirming the presence of the accelerated arrhythmia with a first subcutaneous sense channel during a first time period, and confirming the presence of the accelerated arrhythmia with the first subcutaneous sense channel and a second subcutaneous channel during a second time period following the first time period.

The invention still further provides a circuit for determining heart rate comprising a detector that detects heart beats, and a rate calculator that calculates a heart rate from detected heart beats. The circuit further comprises a timer that begins timing a time period when the heart rate transitions out of a given range and completes timing of the time period when the heart rate returns to within the given range. The circuit still further comprises a rate calculator control that causes the rate calculator to discount the out of range heart rate when the timed time period is less than a predetermined duration.

The given range may be a rate above a first rate and a rate below a second rate. Alternatively, the given range may be a rate below a first rate and a rate above a second rate.

The invention further provides an implantable cardiac stimulation device comprising a sensing circuit that senses heart beats, a heart rate calculator that calculates heart rate, and an accelerated arrhythmia detector that compares the calculated heart rate to a standard to detect an accelerated arrhythmia. The device further comprises a timer that times a time period when the heart rate is outside of a given range, a calculator control responsive to the timer that causes the heart rate calculator to ignore heart rate values occurring during the timed time period when the time period is less than a given duration, and a therapy circuit that applies stimulation therapy to the heart responsive to the accelerated arrhythmia detector detecting an accelerated arrhythmia.

The method further provides a method of determining heart rate comprising detecting heart beats, calculating a heart rate from detected heart beats, timing a time period when the heart rate is outside a given range, and discounting the out of range heart rate when the timed time period is less than a predetermined duration.

The invention still further provides a method of stimulating a heart comprising, sensing heart beats, calculating heart rate from the sensed heart beats, and comparing the calculated heart rate to a standard to detect an accelerated arrhythmia. The method further comprises timing a time period when the heart rate is outside of a given range, ignoring, for heart rate calculation, heart rate values occurring during the timed time period when the timed time period is less than a given duration, and applying stimulation therapy to the heart responsive to detecting an accelerated arrhythmia.

BRIEF DESCRIPTION OF THE DRAWINGS

Further features and advantages of the present invention may be more readily understood by reference to the following description taken in conjunction with the accompanying drawings, in which.

DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
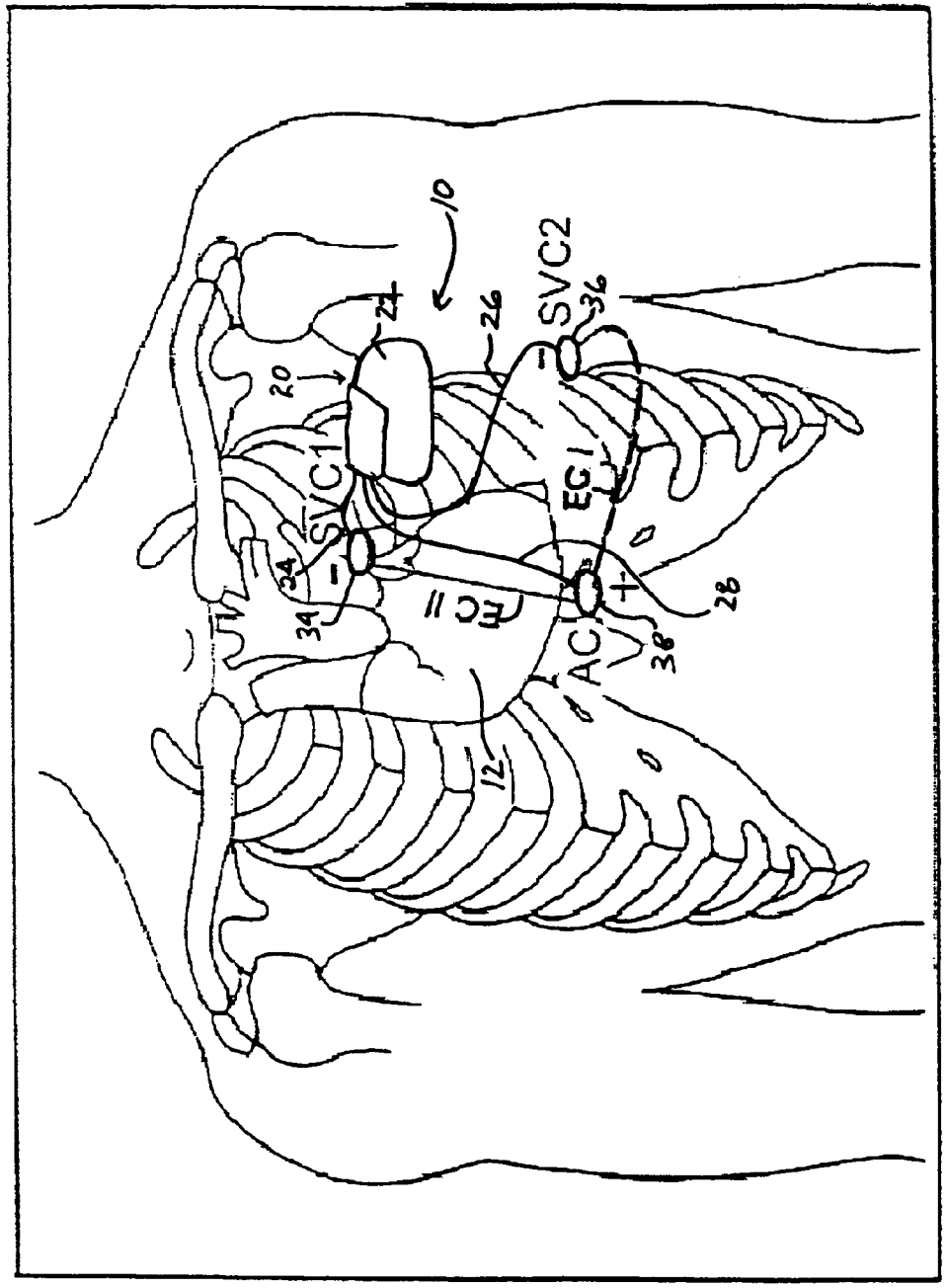
FIG. 1 is a simplified diagram illustrating a subcutaneous defibrillation system embodying the present invention in association with a patient's heart to be treated in accordance with the present invention.

As shown in FIG. 1, there is a subcutaneous cardiac stimulation system 10 shown in association with a patient's heart 12 for delivering shock therapy to the heart 12. The system 10 comprises a subcutaneous defibrillator 20 which may be placed subcutaneously near the third rib next to the sternum.

The defibrillator 20 includes a case or enclosure 22, a first subcutaneous lead 24 having electrode 34, a second subcutaneous lead 26 having electrode 36, and a third subcutaneous lead 28 having electrode 38. The subcutaneous electrodes 34, 36 and 38 are placed to provide two sensing vectors across the heart. The first vector (ECI) is oriented with a negative pole (electrode 36) overlying the posterior left ventricular apex and the positive pole (electrode 38) overlying the inferior aspect of the right ventricle. The second vector (EC II) is oriented with a negative pole (electrode 34) overlying the superior aspect of the left atrium and shares the positive pole with vector ECI (electrode 38).

The defibrillator 20 preferably includes all the hardware circuitry and software to sense electrical activity of the heart 12, to detect therefrom accelerated arrhythmias of the heart, such a ventricular fibrillation requiring high voltage shock therapy from a shocking circuit or ventricular tachycardia requiring a lesser shock or anti-tachycardia pacing pulses from a pulse generator. Any pair of the electrodes 34, 36 and 38 may be employed for sensing electrical activity of the heart 12. As will be seen subsequently, two sensing vectors are employed for accelerated arrhythmia detection verification. To that end, vectors EC1 and EC11 may be used and hence electrodes 36 and 38, and 34 and 38. Any combination of the electrodes 34, 36 and 38 and the case 22 may be used for delivering defibrillating shocks or pacing pulses to the heart 12.

Figure 2:
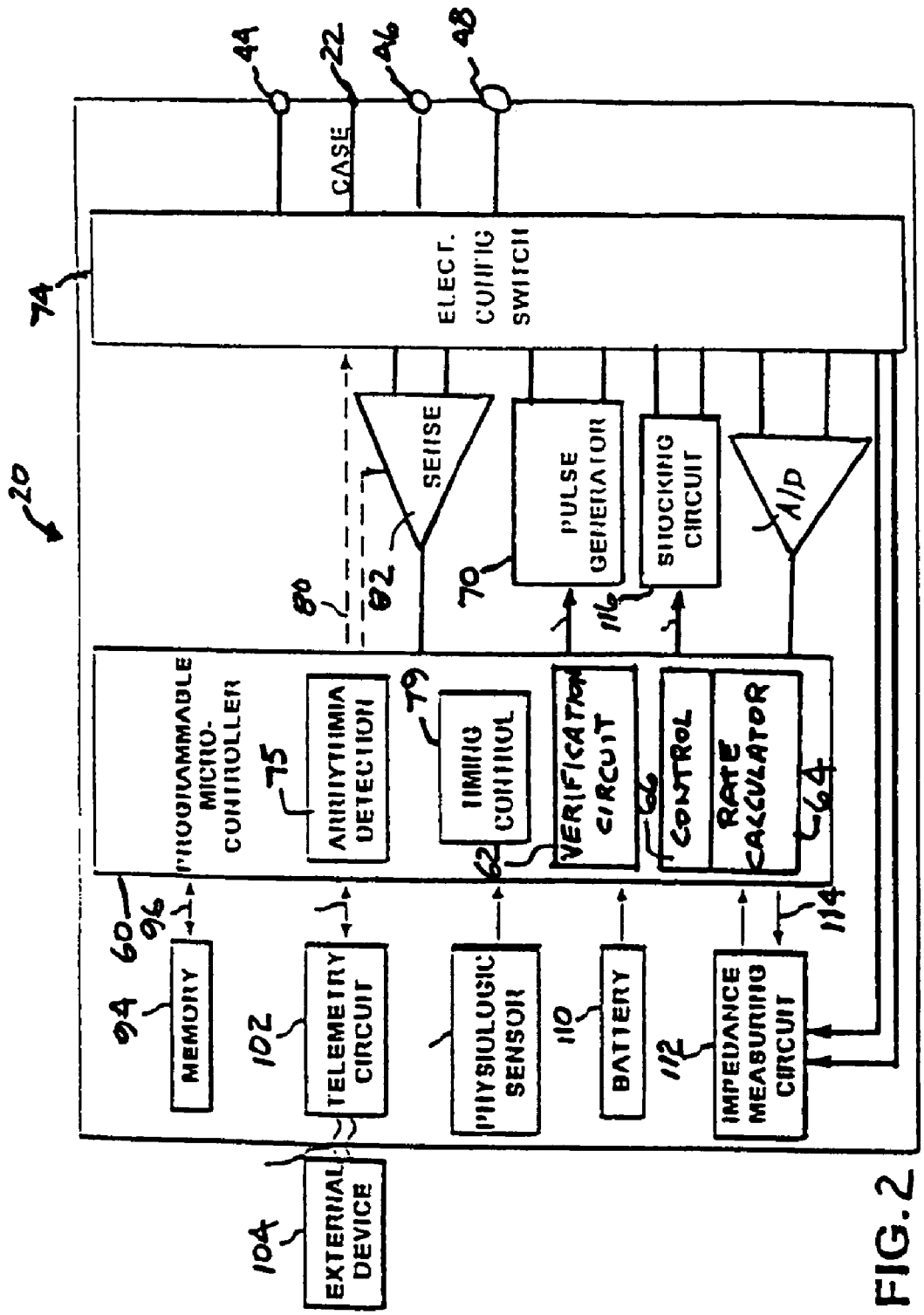
FIG. 2 is a functional block diagram of the subcutaneous device of FIG. 1 according to one embodiment of the invention.

Referring now to FIG. 2, it is a simplified block diagram of the circuitry of the subcutaneous defibrillator 20. The enclosure or case 22 for the stimulation device circuitry is shown schematically and may be conductive and programmably selected to act as a return electrode alone or in combination with one or more of the electrodes 34, 36 and 38 for cardioversion or defibrillation purposes. The enclosure further includes a connector (not shown) having terminals 44, 46, and 48 for connection to electrodes 34, 36, and 38 respectively.

At the core of the subcutaneous stimulation device 20 is a programmable microcontroller 60 which controls the stimulation therapy. The microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As further shown in FIG. 2, a pulse generator 70 generates anti-tachycardia pacing stimulation pulses for delivery by selected ones of electrodes 34, 36, and 38 via an electrode configuration switch 74. The switch 74 includes a plurality of switches for connecting the desired electrodes to the appropriate I/O circuits. The switch 74 operates in response to a control signal 80 from the microcontroller 60 for making the desired electrode connections.

The microcontroller 60 further includes timing control circuitry 79. The timing control circuitry 79 is used to control the timing of defibrillation shocks or stimulation pulses as well as timing various time periods to be described subsequently.

A sensing circuit 82 may also be selectively coupled to desired ones of the electrodes through the switch 74 for detecting the presence of cardiac activity. It may include dedicated sense amplifiers, multiplexed amplifiers, or shared amplifiers.

The sensing circuit 82 preferably employs one or more low power, precision amplifiers with programmable gain and/or automatic gain control, bandpass filtering, and a threshold detection circuit, as known in the art, to selectively sense the cardiac signal of interest. The automatic gain control thus enables the defibrillator 20 to reliably sense the ventricular cardiac activity to support detection of tachycardia and fibrillation. The output of the sensing circuit 82 is connected to the microcontroller 60.

The device 20 further includes an arrhythmia detector 75 that utilizes the sensing circuit 82 to sense cardiac signals to determine whether an accelerated arrhythmia is present. Again, as used herein "sensing" is reserved for the noting of an electrical signal, and "detection" is the processing of these sensed signals and noting the presence of an arrhythmia. The timing intervals between sensed events are used to calculate a cardiac rate which is classified by the microcontroller 60 by comparing them to predefined rate zone limits and, together with other characteristics including myopotential and power, determines the presence of a sustained tachycardia or fibrillation requiring anti-tachycardia pacing or defibrillation shocks, respectively.

The microcontroller 60 is further coupled to a memory 94 by a suitable data/address bus 96, wherein the programmable operating parameters used by the microcontroller 60 are stored and modified, as required, in order to customize the operation of the subcutaneous defibrillator 20 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart.

Advantageously, the operating parameters of the defibrillator 20 may be non-invasively programmed into the memory 94 through a telemetry circuit 102 in telemetric communication with an external device 104, such as a programmer, transtelephonic transceiver, or a diagnostic system analyzer.

As further shown in FIG. 2, the device 20 is shown as having an impedance measuring circuit 112 which is enabled by the microcontroller 60 via a control signal 114. The known uses for an impedance measuring circuit 112 include, but are not limited to, lead impedance surveillance, detection of operable electrodes and automatically switching to an operable pair if necessary, or determining shock thresholds.

The subcutaneous defibrillator further includes a shocking circuit 116. The shocking circuit 116 preferably generates shocking pulses of between 200 and 2,000 volts and more preferably between 500 and 1,000 volts for defibrillation.

Upon detection of fibrillation, the charging circuit (not shown) is called upon to charge an output capacitor (not shown) to a desired high voltage. Then, the arrhythmia detector redetects to verify the fibrillation detection. Once the fibrillation detection is verified, the shocking circuit 116 applies a defibrillation shock from the output capacitor to the desired ones of electrodes 34, 36, and 38.

The subcutaneous defibrillator 20 additionally includes a battery 110 which provides operating power to all of the circuits shown in FIG. 2. The battery may be a lithium/silver vanadium oxide battery.

As previously mentioned, before the device 20 delivers a defibrillation shock, the detection of the accelerated arrhythmia, such as ventricular fibrillation, is verified. To this end, as will be seen in FIG. 2, the device 20 includes a verification circuit 62. The verification circuit 62 utilizes the arrhythmia detector 75 to verify that the accelerated arrhythmia is present. In accordance with this embodiment, the verification circuit 62 utilizes the detection sense channel (EC1) employing electrodes 36 and 38 and hereinafter referred to as the first channel. It also employs the sense detection channel (EC2) employing electrodes 34 and 38 and hereinafter referred to as the second channel. The manner in which the verification circuit 62, in accordance with this embodiment, verifies the presence of the ventricular fibrillation is described in the flow chart of FIG. 3.

Figure 3:
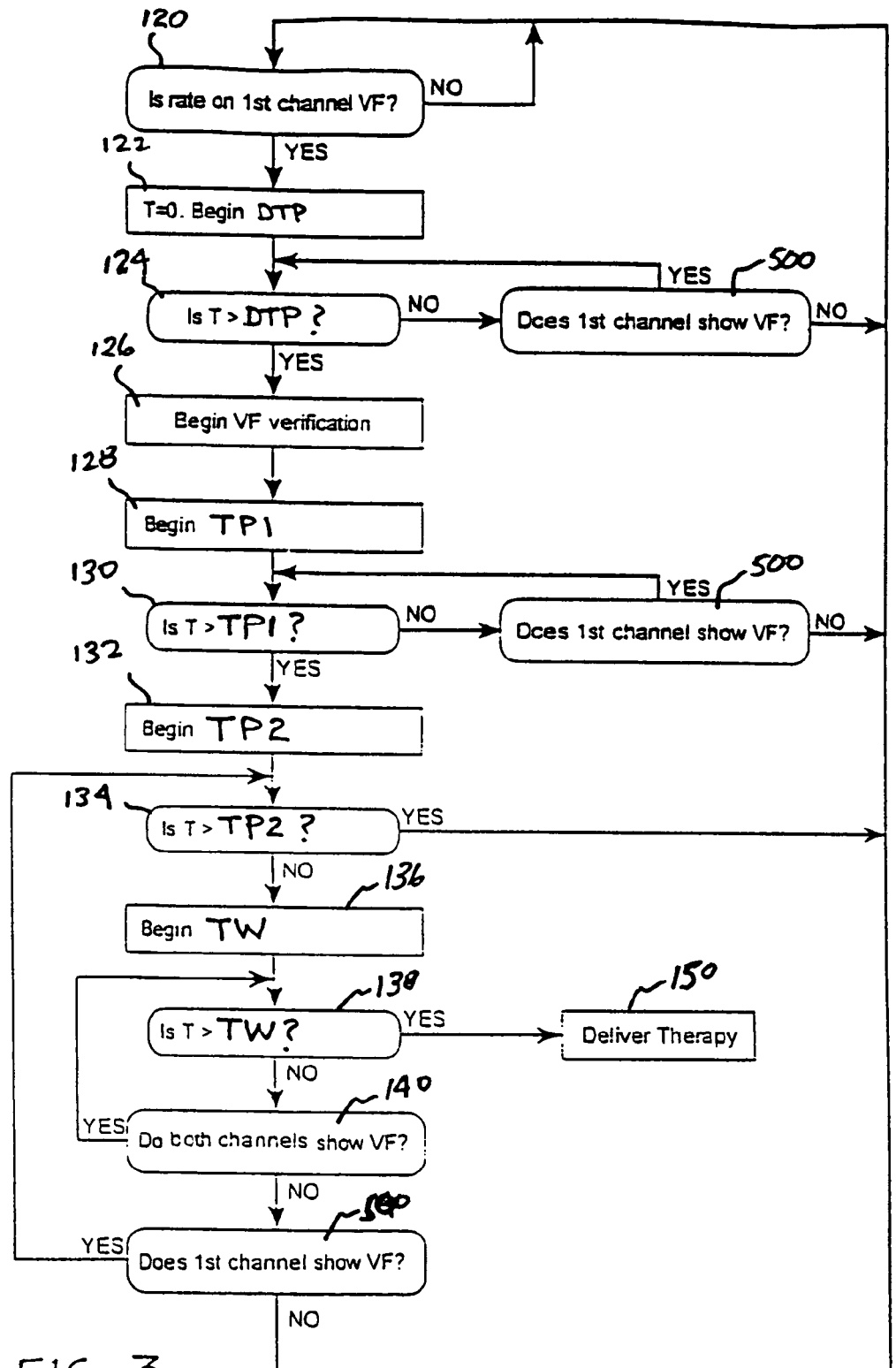
FIG. 3 is a flow chart describing an arrhythmia detection verification embodiment of the present invention.

In FIG. 3, a flow chart is shown describing an overview of the operation and novel feature implemented in one embodiment of the device 20 for verifying the accelerated arrhythmia detection. In this flow chart, and the other flow charts described herein, the various algorithmic steps are summarized in individual "blocks". Such blocks describe specific actions or decisions that must be made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

In order to detect fibrillation in both the first and second channels, the sense amplifier 82 of FIG. 2 may be multiplexed as previously described. The multiplexed signals may then be utilized by a rate calculator 64 which calculates the cardiac rate. A rate calculator control 66, to be described hereinafter, accommodates or compensates for transient changes in the detected cardiac rates.

Figure 4:
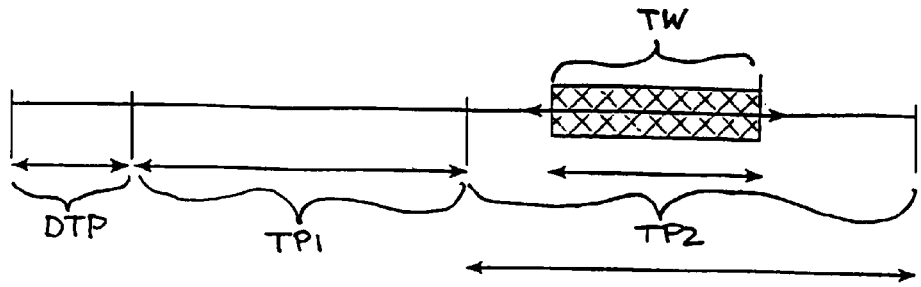
FIG. 4 is a timing diagram of the embodiment of FIG. 3.

During the description of FIG. 3, reference may also be made to the timing diagram of FIG. 4 which may lend a better understanding of the various verification time periods and windows carried out in implementing this embodiment of the present invention. Also, a first channel is utilized to verify the accelerated arrhythmia during a first time period followed by a second time period wherein both the first and second channels are called upon to each verify the presence of the accelerated arrhythmia. The channel designated the first channel in implementing the accelerated arrhythmia detection verification may be either the channel which first detects the presence of the accelerated arrhythmia or a default channel such as the channel comprising electrodes 36 and 38 (EC1) or the channel comprising electrodes 34 and 38 (EC2). For purposes of this discussion, it will be assumed that the first channel of the flow chart of FIG. 3 is the channel (EC1) comprising electrodes 36 and 38.

The process of FIG. 3 initiates with decision block 120 wherein it is determined if the cardiac rate on the first channel is a rate which indicates the accelerated arrhythmia, in this case ventricular fibrillation. As will be seen hereinafter, the rate criteria for detecting ventricular fibrillation calls for either a rate which is greater than a first rate (TH) or a rate which is less than a second rate (TL), where TH is greater than TL. If the rate does not indicate ventricular fibrillation (VF), the process returns. If the rate does indicate VF, the process then advances to activity block 122 wherein the timing control 79 is called upon to begin timing a diagnosis time period (DTP). The process then advances to decision block 124 wherein it is determined if the time on the timer is greater than the diagnosis time period. If it is not, the process then advances to decision block 500 wherein it is determined if the activity sensed on the first channel is indicative of the presence of VF. The process performed in implementing decision block 500 will be described with greater detail with reference to FIG. 5 hereinafter. If the cardiac activity sensed with the first channel does not indicate VF, the process returns. However, if it does, the process then returns to decision block 124. When the diagnosis time period completes, and if during the diagnosis time period the sensed cardiac activity on the first channel continuously indicated VF, the process then advances to activity block 126 wherein the verification of the accelerated arrhythmia is initiated.

The verification begins with activity block 128 wherein the timing control 79 begins timing the first time period (TP1). The process then advances to decision block 130 wherein it is determined if the time on the timing control is greater than the first time period duration. If it is not, the process advances to repeat decision block 500 to determine if the cardiac activity on the first channel is indicative of VF. If it is not, the process returns. If it is, the process returns to decision block 130. At the end of the first time period (TP1), and if during the first time period the cardiac activity sensed on the first channel continuously indicated the presence of VF, the process then advances to activity block 132 where the timing control begins timing the second time period (TP2). The process then advances to decision block 134 wherein it is determined if the time on the timing control is greater than the second time period (TP2). If the second time period has not yet completed, the process then begins the time window (TW) in accordance with activity block 136. The process then advances to decision block 138 where it is determined if the timing window has expired. If it has not, the process then advances to decision block 140 where it is determined if both the first and second channels are sensing cardiac activity indicative of VF. The manner in which the second channel determines if the cardiac signal sensed with its electrodes indicate VF will be described in greater detail with reference to FIG. 6 subsequently.

If both channels indicate VF, the process returns to decision block 138 to determine if the time window has expired. If the time window has not expired, the process then repeats decision block 140 to determine if both channels indicate VF. If both channels have indicated VF continuously through the timing window (TW), the detection of the ventricular fibrillation is considered verified and the process advances to activity block 150 wherein the shock therapy for defibrillating the ventricles is applied or delivered to the heart.

If, however, in decision block 140 it was determined that both channels do not indicate VF, the process then advances to repeat decision block 500 to determine if the activity sensed with the first channel indicates VF. If it does, the process then returns back to decision block 134 wherein it is determined if the timing control has completed the timing of the second time period TP2. If it has, the process returns without accelerated arrhythmia detection being verified. However, if the second time period has not yet expired, the process then advances to activity block 136 for once again beginning the time window TW. If in repeating decision block 500 after decision block 140 it is determined that the first channel does not indicate VF, the process returns since in that event, both the first channel and the second channel would indicate that the VF is not present.

As will be noted in the foregoing discussion with respect to FIG. 4, the first channel is utilized to verify the presence of the accelerated arrhythmia during the first time period TP1. Following the first time period, during the second time period TP2, both the first channel and the second channel must continuously verify the existence of the VF until the timing window TW has completed. If the second channel fails to continuously verify the VF detection, the timing window is restarted when the second channel once again detects the ventricular fibrillation, assuming that the second time period TP2 has not yet expired. Hence, as can be seen, the timing window TW in which the second channel must continuously verify the existence of the ventricular fibrillation is a floating or sliding window. The ventricular fibrillation detection is verified, then, if the second channel continuously verifies the ventricular fibrillation detection during the time window TW, if the first channel continuously verifies the ventricular fibrillation from the beginning of the second time period until the end of the timing window, and if the timing window has not expired before completion of the second time period TP2. If all of these conditions are satisfied, the ventricular fibrillation detection is verified and the shock therapy is delivered.

Figure 5:
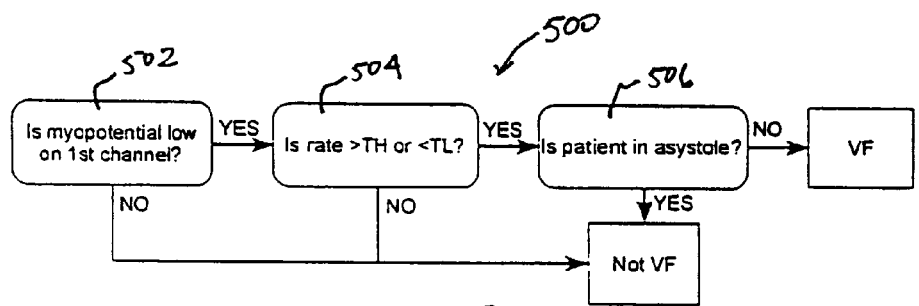
FIG. 5 is a flow chart describing a first accelerated arrhythmia detection embodiment of the present invention.

Referring now to FIG. 5, it is a flow chart describing the manner in which the first channel may verify the presence of ventricular fibrillation in accordance with this embodiment of the present invention. The process 500 of FIG. 5 begins with decision block 502 wherein it is determined if the myopotential is low on the first channel. As is well known in the art, myopotential is an electrical signal originating in muscle tissue which may be caused by voluntary or involuntary movement. If the myopotential measure is above a given threshold, it may be assumed that the patient is exercising and that the higher cardiac rate is due to the exercise and not due to an accelerated arrhythmia. Hence, if the myopotential is not low, it is determined that there is no ventricular fibrillation. However, if the myopotential is below the given threshold, the process then advances to decision block 504 wherein it is determined if the cardiac rate is greater than the first rate TH or less than a second rate TL, where TH is greater than TL. If it is not, once again ventricular fibrillation is determined to not exist. However, if the rate satisfies the criteria of decision block 504, the process advances to decision block 506 wherein it is determined if the patient is in asystole. Asystole may be determined by a power calculation of the type known in the art, or using any other method. The power calculation should result in a higher factor during VF and a lesser factor during asystole. Asystole is the condition where the heart rate is absent. If asystole is considered to be present in decision block 506, it is determined that there is no ventricular fibrillation. However, if a high power factor results, it is determined that asystole is not present and that all of the conditions have been satisfied for the detection of ventricular fibrillation.

Figure 6:
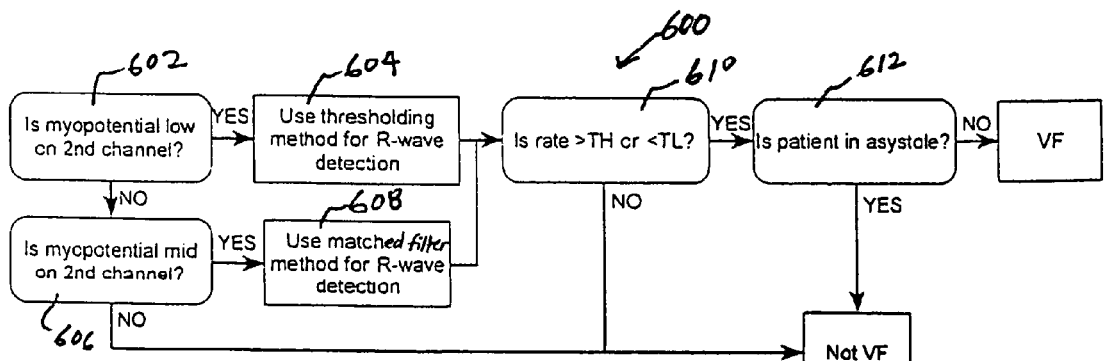
FIG. 6 is a flow chart describing a second accelerated arrhythmia detection embodiment of the present invention.

Referring now to the flow chart of FIG. 6, it describes the manner in which the second channel may be utilized for detecting ventricular fibrillation. The process 600 of FIG. 6 begins with decision block 602 wherein it is determined if the myopotential on the second channel is low. If the myopotential on the second channel is low, the process advances to activity block 604 wherein a thresholding method is utilized for determining cardiac rate. If, however, in decision block 602 it is determined that the myopotential on the second channel is not low, the process advances to decision block 606 where it is determined if the myopotential is in a mid range. If the myopotential is not in a mid range, it is assumed that the myopotential is high, and that therefore, the subject is exercising and there is no ventricular fibrillation. However, if it is determined that the myopotential on the second channel is in a mid range the process advances to activity block 608 wherein a matched filter method is utilized for calculating the cardiac rate. The thresholding method of activity block 604 and the matched filter method of activity block 608 are fully described in the aforementioned U.S. Pat. No. 7,403,813 and copending application Ser. No. 10/998,027.

The cardiac rate determined in the appropriate activity block 604 or 608 is then utilized in decision block 610. Here it is determined if the calculated rate is greater than the first rate TH or less than the second rate TL. If the cardiac rate does not satisfy this criteria, then it is determined that there is not ventricular fibrillation. However, if the cardiac rate satisfies the criteria, the process advances to decision block 612 where it is determined if the patient is in asystole. Activity block 612 may be implemented in the same manner as activity block 506 of FIG. 5. If the patient is in asystole, it is determined that VF is not present. However, if the patient is not in asystole, then the ventricular fibrillation detection is confirmed.

In some instances, it may be desirable to perform the verification process without the asystole check. Still further, another embodiment may be implemented wherein if the second channel has a myopotential in the mid range, it is also assumed that the patient is not in VF and that a defibrillation shock should not be delivered.

Figure 7:
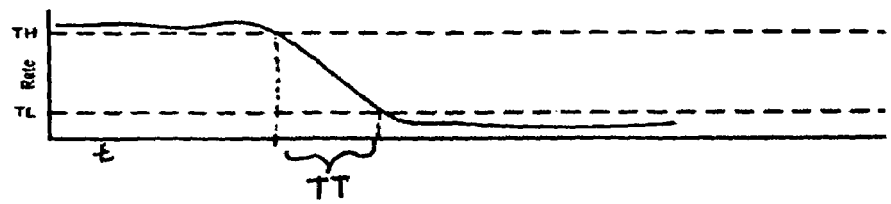
FIG. 7 is a plot of cardiac rate versus time to illustrate a first transient rate change which may be accommodated according to an embodiment of the invention.

As previously mentioned, in detecting an accelerated arrhythmia such as ventricular tachycardia or ventricular fibrillation with subcutaneous electrodes transient cardiac rates may occur. This is due to high signal amplitude variability in surface or subcutaneous cardiac activity recordings. To compensate for this, the present invention is further directed to a method of determining when transient rate changes occur and then, depending on the duration of the transient condition, it is determined whether the transient rate change should be taken into account in calculating the cardiac rate. FIGS. 7-10 illustrate the four possible cases in which transient rate compensation may be required when detecting for ventricular fibrillation. A first case is depicted in FIG. 7 where the cardiac rate begins above the first rate TH but then transitions to a rate less than the second rate TL. The transition time (TT) is indicated in the figure.

Figure 8:
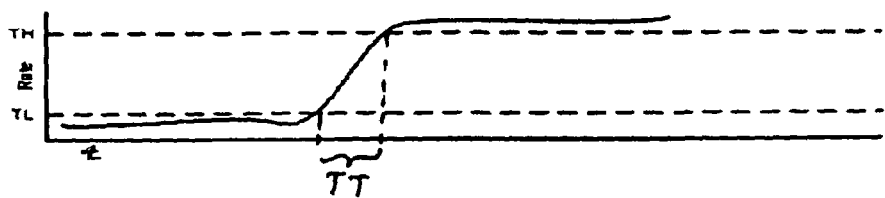
FIG. 8 is a plot of cardiac rate versus time to illustrate a second transient rate change which may be accommodated according to an embodiment of the invention.

FIG. 8 illustrates the second case in which the transient rate compensation may be necessary when detecting for ventricular fibrillation. Here it may be noted that the cardiac rate transitions from a rate less than the second rate TL to a rate greater than a first rate TH. Again, the transition time TT is indicated in the figure.

Figure 9:
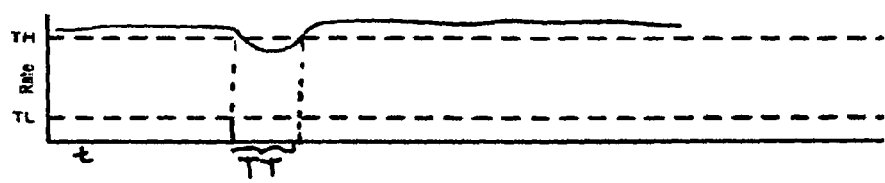
FIG. 9 is a plot of cardiac rate versus time to illustrate a third transient rate change which may be accommodated according to an embodiment of the invention.

FIG. 9 illustrates the third case in which the transient rate compensation may be required during detection for VF. Here it may be seen that the cardiac rate transitions from a rate above the first rate TH to below the first rate TH and then back above the first rate TH. Again, the transition time TT is indicated in the figure.

Figure 10:
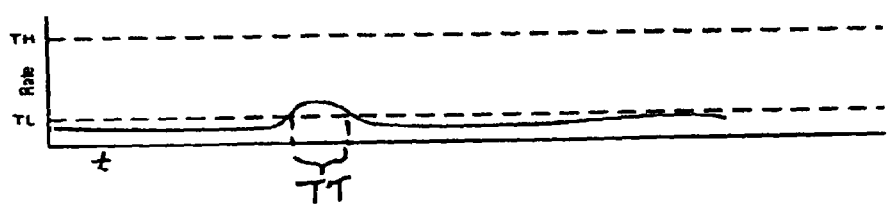
FIG. 10 is a plot of cardiac rate versus time to illustrate a fourth transient rate change which may be accommodated according to an embodiment of the invention.

Lastly, FIG. 10 illustrates the fourth case in which the transient rate change compensation may be required. Here, it may be seen that the rate transitions from a rate below the second rate TL, to a rate above the second rate TL but below the first rate TH, and then back to a rate which is less than TL. The transition time TT is once again indicated in the figure.

Figure 11:
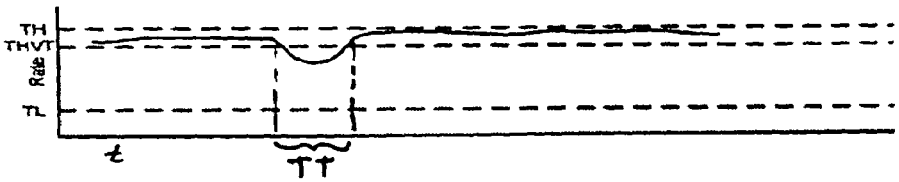
FIG. 11 is a plot of cardiac rate versus time to illustrate a fifth transient rate change which may be accommodated according to an embodiment of the invention.

FIG. 11 indicates a case wherein transient rate compensation may be required during detection for ventricular tachycardia. Here, it may be seen that the rate begins in a tachycardia rate which is above a third rate THVT but below the first rate TH, to a rate less than THVT but greater than the second rate TL, and then returns to a rate less than TH but greater than THVT. The transition time TT is indicated in the figure.

Figure 12:
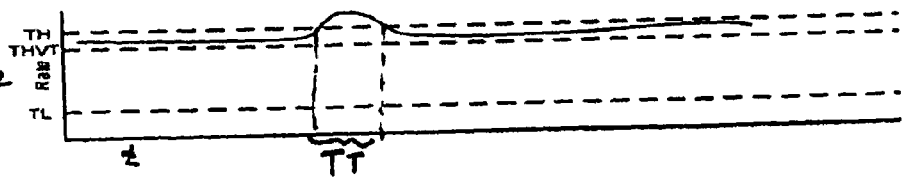
FIG. 12 is a plot of cardiac rate versus time to illustrate a sixth transient rate change which may be accommodated according to an embodiment of the invention.

Lastly, FIG. 12 illustrates a second case where transient rate compensation may be required in detecting ventricular tachycardia. Here it may be noted that the rate begins with a rate less than the first rate TH but greater than the third rate THVT, transitions to a rate greater than the first rate TH, and then returns back to a rate between the first rate TH and the third rate THVT. Again, the transition time TT is indicated in the figure. In each of the six cases illustrated in FIGS. 7-12, transient rate compensation may be required. The flow chart of FIG. 13 indicates when such transient rate change compensation is required and should be taken into account when calculating cardiac rate.

Figure 13:
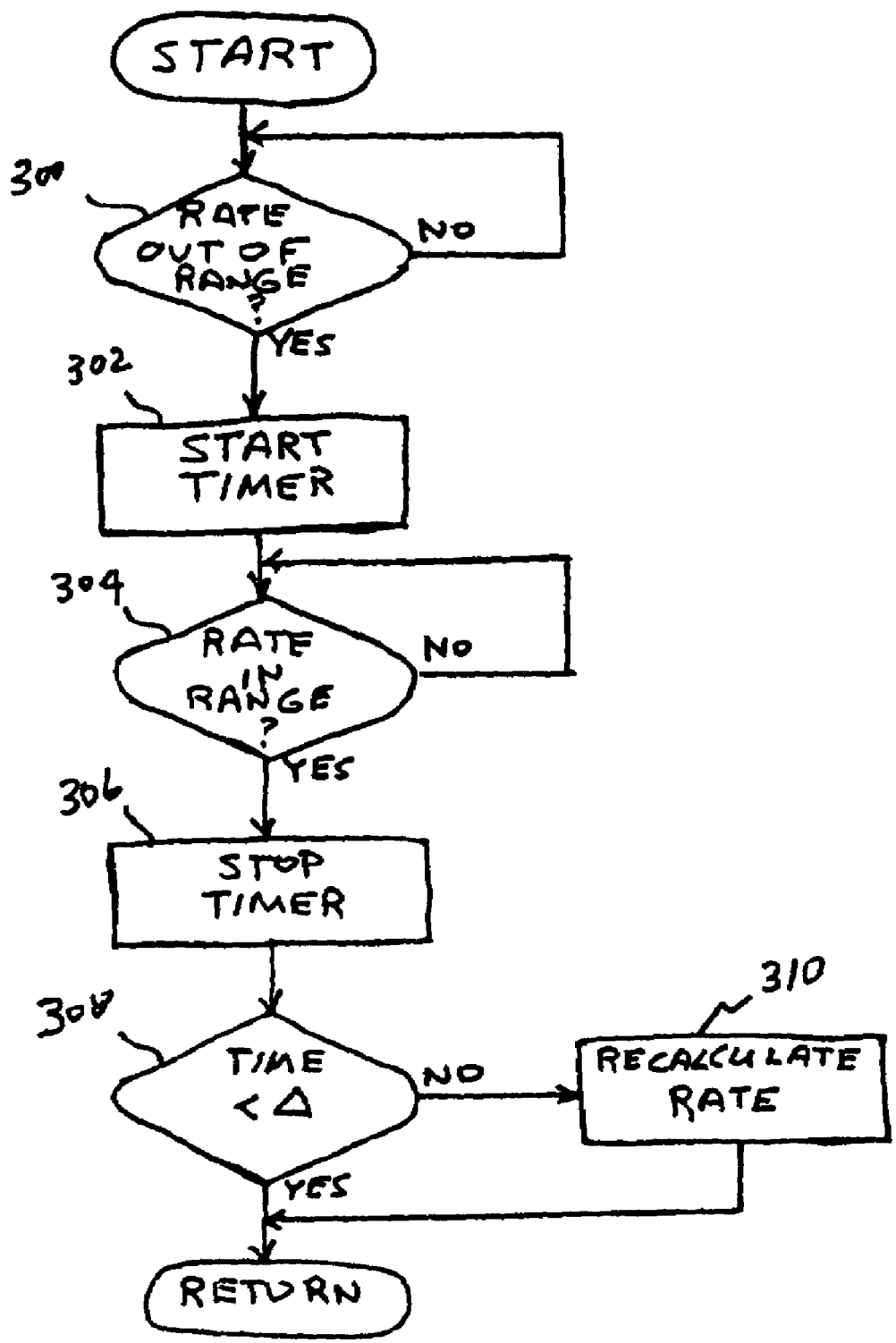
FIG. 13 is a flow chart describing an overview of the operation of a transient rate change compensation embodiment of the present invention.

The process of FIG. 13 begins with decision block 300 wherein it is determined by the rate calculator control 66 if the cardiac rate is out of a given range. For VF detection, the given range is greater than the first rate TH or less than a second rate TL. For ventricular tachycardia detection, the range would be a rate less than the first rate TH but greater than the third rate THVT. If the cardiac rate is not out of range, the process returns. However, if the cardiac rate is out of range, the process then advances to activity block 302 wherein the timing control starts a timer. The process then advances to decision block 304 wherein it is determined if the cardiac rate has returned to be within range. If it hasn't, the process continues to look for the cardiac rate returning to within the given range. If, however, the cardiac rate is determined to have returned to the given range in decision block 304, the timer of the timing control 79' is stopped in activity block 306. The process then advances to decision block 308 wherein it is determined if the timed time period, the time in which the cardiac rate was out of range, is less than a given time period $\Delta$. If the timed time period is less than $\Delta$, the heart rate values calculated during the timed time period are discounted or ignored in determining cardiac rate. The process returns. However, if the transition time in which the cardiac rate was out of range is greater than $\Delta$, the heart rate values during the timed time period are not ignored or discounted and a new cardiac rate is calculated in accordance with activity block 310. The process then returns.

Hence, as can be seen from the foregoing, there may be two thresholds used to diagnose ventricular fibrillation, a low threshold (TL) and a high threshold (TH). Ventricular fibrillation is diagnosed if the rate is either below TL or above TH for a given period of time. However, if the rate falls out of that range for less than a predetermined time period, the cardiac rate values during the out of range time period are ignored.

Similarly, diagnosis of ventricular tachycardia may require that the rate be below the VF rate of TH but above a ventricular tachycardia rate THVT. Again, if the rate falls out of this range, transient rate compensation may be required. If the out of range time period is less than a predetermined time period $\Delta$, the out of range rate values during the timed time period are ignored for the cardiac rate calculation. However, if the timed time period during which the cardiac rate was out of range is greater than a predetermined time period, the out of range rate values calculated during the timed time period are taken into account and a new cardiac rate is calculated.

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What is claimed is:

1. A subcutaneous cardiac stimulation system comprising:
an arrhythmia detector that detects an accelerated arrhythmia of a heart;
a subcutaneous lead system coupled to the arrhythmia detector and defining first and second arrhythmia detection electrode configurations;
a verification circuit that verifies detection of an accelerated arrhythmia with each of the first and second arrhythmia detection electrode configurations; and
a therapy circuit that delivers stimulation therapy to the heart responsive to verification of an accelerated arrhythmia with each of the first and second arrhythmia detection electrode configurations;
wherein the verification circuit is responsive to a first detection of an accelerated arrhythmia with a first one of the first and second arrhythmia detection electrode configurations;
wherein the verification circuit first verifies an accelerated arrhythmia detection with the first one of the first and second arrhythmia detection electrode configurations;
wherein the verification circuit first verifies an accelerated arrhythmia detection with the first one of the first and second accelerated arrhythmia detection electrode configurations during a first verification time period following the first detection of the accelerated arrhythmia;
wherein the verification circuit further verifies the accelerated arrhythmia detection with both the first and second accelerated arrhythmia detection electrode configurations during a further verification period following the first verification period; and
wherein the verification circuit verifies the accelerated arrhythmia detection during the further verification period with a second one of the first and second accelerated arrhythmia detection electrode configurations providing continuous accelerated arrhythmia detection verification during a verification window within the further verification period.

2. The system of claim 1 wherein the verification window is a floating window.

3. The system of claim 1 wherein the further verification is completed upon continuous verification with the first one of the first and second accelerated arrhythmia detection electrode configurations up to completion of the verification window.

4. The system of claim 1 wherein the therapy circuit delivers the stimulation therapy to the heart following the further verification.

5. The system of claim 1 wherein the accelerated arrhythmia is ventricular fibrillation.

6. The system of claim 1 wherein the accelerated arrhythmia is ventricular tachycardia.

7. The system of claim 1 wherein the verification circuit verifies detection of an accelerated arrhythmia based upon heart rate.

8. A subcutaneous cardiac stimulation system comprising:
an arrhythmia detector that detects an accelerated arrhythmia of a heart;
a subcutaneous lead system coupled to the arrhythmia detector and defining first and second arrhythmia detection electrode configurations;
a verification circuit that verifies detection of an accelerated arrhythmia with each of the first and second arrhythmia detection electrode configurations; and
a therapy circuit that delivers stimulation therapy to the heart responsive to verification of an accelerated arrhythmia with each of the first and second arrhythmia detection electrode configurations;
wherein the verification circuit is responsive to a first detection of an accelerated arrhythmia with a first one of the first and second arrhythmia detection electrode configurations;
wherein the verification circuit selects a default one of the first and second accelerated arrhythmia detection electrode configurations as the first one of the first and second accelerated arrhythmia detection electrode configurations responsive to first accelerated arrhythmia detection with both the first and second accelerated arrhythmia detection electrode configurations;

wherein the verification circuit first verifies an accelerated arrhythmia detection with the first one of the first and second arrhythmia detection electrode configurations;

wherein the verification circuit first verifies an accelerated arrhythmia detection with the first one of the first and second accelerated arrhythmia detection electrode configurations during a first verification time period following the first detection of the accelerated arrhythmia;

wherein the verification circuit further verifies the accelerated arrhythmia detection with both the first and second accelerated arrhythmia detection electrode configurations during a further verification period following the first verification period; and wherein the verification circuit verifies the accelerated arrhythmia detection during the further verification period with a second one of the first and second accelerated arrhythmia detection electrode configurations providing continuous accelerated arrhythmia detection verification during a verification window within the further verification period.

9. The system of claim 8 wherein the verification window is a floating window.

10. The system of claim 8 wherein the further verification is completed upon continuous verification with the first one of the first and second accelerated arrhythmia detection electrode configurations up to completion of the verification window.

11. A subcutaneous cardiac stimulation system comprising:
 an arrhythmia detector that detects an accelerated arrhythmia of a heart;
 a subcutaneous lead system coupled to the arrhythmia detector and defining first and second arrhythmia detection electrode configurations;
 a verification circuit that verifies detection of an accelerated arrhythmia with each of the first and second arrhythmia detection electrode configurations; and
 a therapy circuit that delivers stimulation therapy to the heart responsive to verification of an accelerated arrhythmia with each of the first and second arrhythmia detection electrode configurations;
 wherein the verification circuit determines absence of asystole to verify detection of an accelerated arrhythmia.

12. A subcutaneous cardiac stimulation system comprising:
 an arrhythmia detector that detects an accelerated arrhythmia of a heart;
 a subcutaneous lead system coupled to the arrhythmia detector and defining first and second arrhythmia detection electrode configurations;
 a verification circuit that verifies detection of an accelerated arrhythmia with each of the first and second arrhythmia detection electrode configurations; and
 a therapy circuit that delivers stimulation therapy to the heart responsive to verification of an accelerated arrhythmia with each of the first and second arrhythmia detection electrode configurations;
 wherein the verification circuit measures myopotential on at least one of the electrode configurations.

13. A subcutaneous cardiac stimulation system comprising:
 an arrhythmia detector that detects an accelerated arrhythmia of a heart;
 a subcutaneous lead system coupled to the arrhythmia detector and defining first and second arrhythmia detection electrode configurations;
 a verification circuit that verifies detection of an accelerated arrhythmia with each of the first and second arrhythmia detection electrode configurations; and
 a therapy circuit that delivers stimulation therapy to the heart responsive to verification of an accelerated arrhythmia with each of the first and second arrhythmia detection electrode configurations;
 wherein the verification circuit measures myopotential on each of the electrode configurations.

14. A method of verifying subcutaneous cardiac accelerated arrhythmia detection comprising:
 confirming presence of the accelerated arrhythmia with a first subcutaneous sense channel during a first time period; and
 confirming presence of the accelerated arrhythmia with the first subcutaneous sense channel and a second subcutaneous channel during a second time period following the first time period;
 wherein the second recited confirming step includes confirming the presence of the accelerated arrhythmia with the second sense channel during a third time period within the second time period; and
 wherein the third time period is a floating time period.

15. The method of claim 14 wherein the step of confirming the presence of the accelerated arrhythmia with the second sense channel includes confirming a continuous presence of the accelerated arrhythmia during the third time period.

16. The method of claim 14 wherein the steps of confirming each includes calculating cardiac rate and comparing the cardiac rate to a standard.

17. The method of claim 14 wherein the confirming steps include measuring myopotential on the first and second subcutaneous sense channels.

18. The method of claim 14 wherein the steps of confirming the presence of the accelerated arrhythmia with the first subcutaneous sense channel include confirming a continuous presence of the accelerated arrhythmia.

19. A method of verifying subcutaneous cardiac accelerated arrhythmia detection comprising:
 confirming presence of the accelerated arrhythmia with a first subcutaneous sense channel during a first time period; and
 confirming presence of the accelerated arrhythmia with the first subcutaneous sense channel and a second subcutaneous channel during a second time period following the first time period;
 wherein the steps of confirming each includes determining an absence of asystole.

* * * * *